United States Patent
Kawata et al.

(10) Patent No.: US 11,207,037 B2
(45) Date of Patent: Dec. 28, 2021

(54) RADIATION DETECTOR AND X-RAY CT APPARATUS

(71) Applicant: CANON MEDICAL SYSTEMS CORPORATION, Otawara (JP)

(72) Inventors: Go Kawata, Nagareyama (JP); Hiroaki Nakai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 42 days.

(21) Appl. No.: 16/878,663

(22) Filed: May 20, 2020

(65) Prior Publication Data

US 2020/0367836 A1 Nov. 26, 2020

(30) Foreign Application Priority Data

May 21, 2019 (JP) .............................. JP2019-095084

(51) Int. Cl.
*A61B 6/03* (2006.01)
*A61B 6/00* (2006.01)

(52) U.S. Cl.
CPC .............. *A61B 6/032* (2013.01); *A61B 6/483* (2013.01); *A61B 6/587* (2013.01)

(58) Field of Classification Search
CPC ......... A61B 6/032; A61B 6/483; A61B 6/587; A61B 6/4021; A61B 6/4291
See application file for complete search history.

(56) References Cited

U.S. PATENT DOCUMENTS

2017/0196524 A1* 7/2017 Koehler ................. A61B 6/542
2017/0212253 A1* 7/2017 Fu ........................ A61B 6/4241

FOREIGN PATENT DOCUMENTS

JP          10-005210 A       1/1998

* cited by examiner

*Primary Examiner* — Courtney D Thomas
(74) *Attorney, Agent, or Firm* — Oblon, McClelland, Maier & Neustadt, L.L.P.

(57) ABSTRACT

A radiation detector according to an embodiment includes a sensor, an electronic circuitry, a switch, and a control circuitry. The sensor configured to be formed of plural electrodes and detect radiation. Based on signals output from the electrodes, the electronic circuitry configured to output digital data. The switch configured to be provided between each of the electrodes and the electronic circuitry. The control circuitry configured to control the switch, based on a positional relation between the plural electrodes and an anti-scatter grid.

9 Claims, 9 Drawing Sheets

RADIATION DETECTOR AND X-RAY CT APPARATUS

CROSS-REFERENCE TO RELATED APPLICATIONS

This application is based upon and claims the benefit of priority from Japanese Patent Application No. 2019-95084, filed on May 21, 2019; the entire contents of which are incorporated herein by reference.

FIELD

Embodiments described herein relate generally to radiation detectors and X-ray computed tomography (hereinafter, "CT") apparatuses.

BACKGROUND

To reduce influence of displacement (misalignment) between a detector module and a collimator in a radiation detector, various techniques have been proposed conventionally. For example, these known techniques include a technique where the degree of misalignment (the amount of displacement) is measured, detected signals are corrected according to the amount of displacement, and an image is thereby reconstructed.

DETAILED DESCRIPTION

A problem to be solved by the present embodiments is to provide a radiation detector and an X-ray CT apparatus that enable reduction of influence of misalignment.

A radiation detector according to an embodiment includes a sensor, an electronic circuitry, a switch, and a control circuitry. The sensor configured to be formed of plural electrodes and detect radiation. Based on signals output from the electrodes, the electronic circuitry configured to output digital data. The switch configured to be provided between each of the electrodes and the electronic circuitry. Based on a positional relation between the plural electrodes and an anti-scatter grid, the control circuitry configured to control the switch.

Hereinafter, radiation detectors and X-ray CT apparatuses according to embodiments will be described by reference to the drawings. The description related to any one of the embodiments is similarly applicable, in principle, to the other embodiments.

With respect to the following embodiments, X-ray detectors will be described as examples, but the embodiments are not limited to these examples. For example, the following embodiments are also applicable to radiation detectors that detect gamma radiation.

Furthermore, with respect to the following embodiments, X-ray CT apparatuses enabling photon-counting CT to be executed will be described as examples, but the embodiments are not limited to these examples. For example, the following embodiments are also each applicable to an X-ray CT apparatus including a charge integrating detector or a radiodiagnostic apparatus including a radiation detector that detects gamma rays.

First Embodiment

Figure 1:
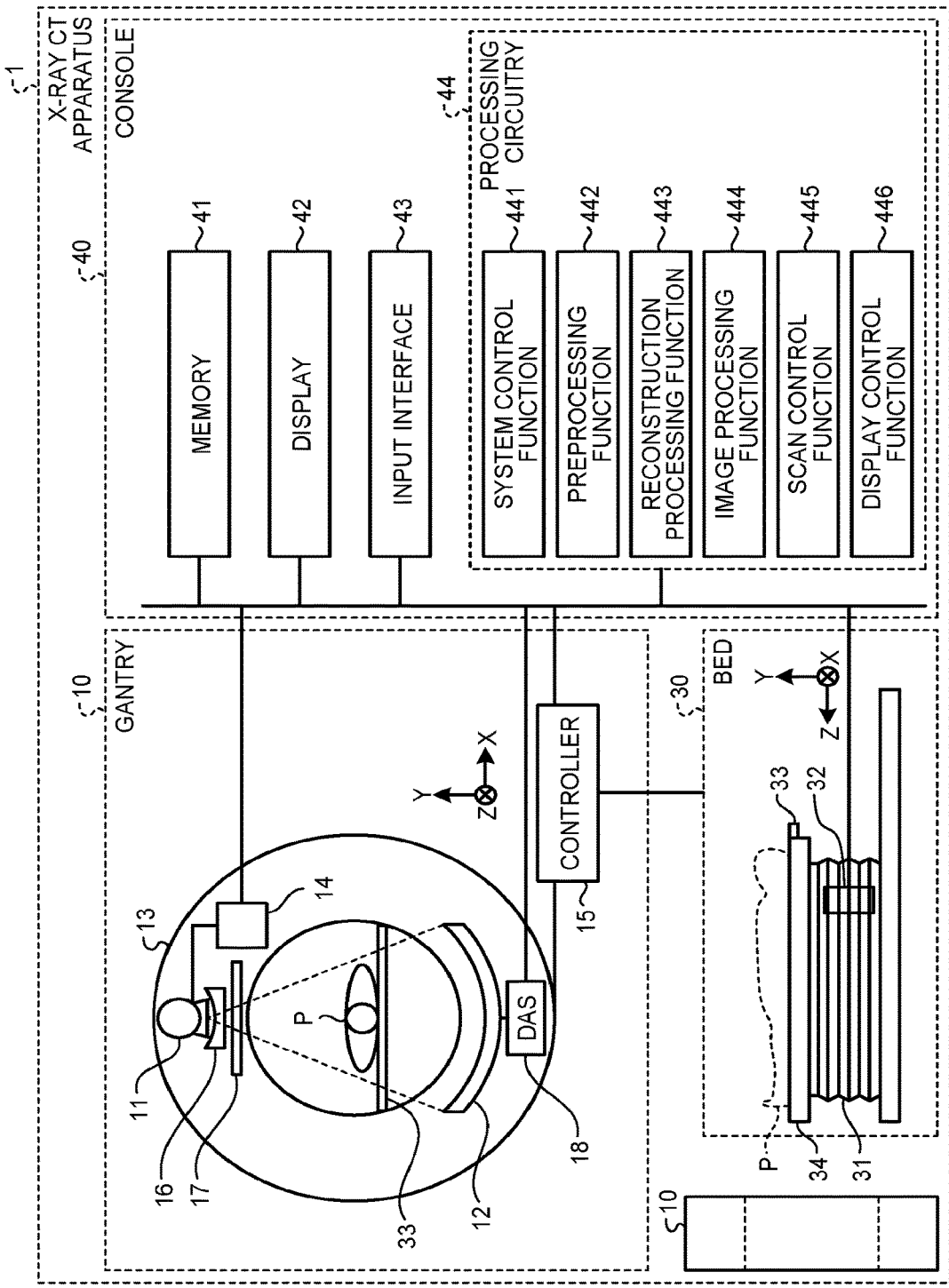
FIG. 1 is a diagram illustrating an example of a configuration of an X-ray CT apparatus according to a first embodiment.

FIG. 1 is a diagram illustrating an example of a configuration of an X-ray CT apparatus 1 according to a first embodiment. As illustrated in FIG. 1, the X-ray CT apparatus according to the first embodiment has a gantry 10, a bed 30, and a console 40.

In FIG. 1, the rotation axis of a rotating frame 13 in a non-tilted state or a longitudinal direction of a tabletop 33 of the bed 30 will be referred to as a Z-axis direction. Furthermore, an axial direction orthogonal to the Z-axis direction and horizontal to a floor surface will be referred to as an X-axis direction. In addition, an axial direction orthogonal to the Z-axis direction and vertical to the floor surface will be referred to as a Y-axis direction. FIG. 1 has the gantry 10 drawn from plural directions for explanation, and illustrates a case where the X-ray CT apparatus 1 has one gantry 10.

The gantry 10 has an X-ray tube 11, an X-ray detector 12, the rotating frame 13, an X-ray high voltage generator 14, a controller 15, a wedge 16, an X-ray diaphragm 17, and a data acquisition system (DAS) 18.

The X-ray tube 11 is a vacuum tube having: a cathode (a filament) that generates thermions; and an anode (a target) that receives collision of the thermions and generates X-rays. The X-ray tube 11 generates X-rays, with which a subject P is irradiated, by emitting thermions from the cathode to the anode through application of high voltage from the X-ray high voltage generator 14. For example, the X-ray tube 11 may be a rotating anode X-ray tube that generates X-rays by irradiation of a rotating anode with thermions.

The rotating frame 13 is an annular frame that supports the X-ray tube 11 and the X-ray detector 12 oppositely to each other and rotates the X-ray tube 11 and the X-ray detector 12 by means of the controller 15. For example, the rotating frame 13 is a casting made of a material including aluminum. The rotating frame 13 may further support, in addition to the X-ray tube 11 and the X-ray detector 12: the X-ray high voltage generator 14; the wedge 16; the X-ray diaphragm 17; and/or the DAS 18. Furthermore, the rotating frame 13 may further support any of various components not illustrated in FIG. 1.

The wedge 16 is a filter for adjusting the X-ray dose for irradiation by the X-ray tube 11. Specifically, the wedge 16 is a filter that transmits and attenuates therethrough X-rays emitted from the X-ray tube 11 so that the subject P is irradiated by the X-ray tube 11 with X-rays having a predetermined distribution. For example, the wedge 16 may be a wedge filter or a bow-tie filter, which is made of aluminum that has been processed to achieve a predetermined target angle and/or have a predetermined thickness.

Figure 2A:
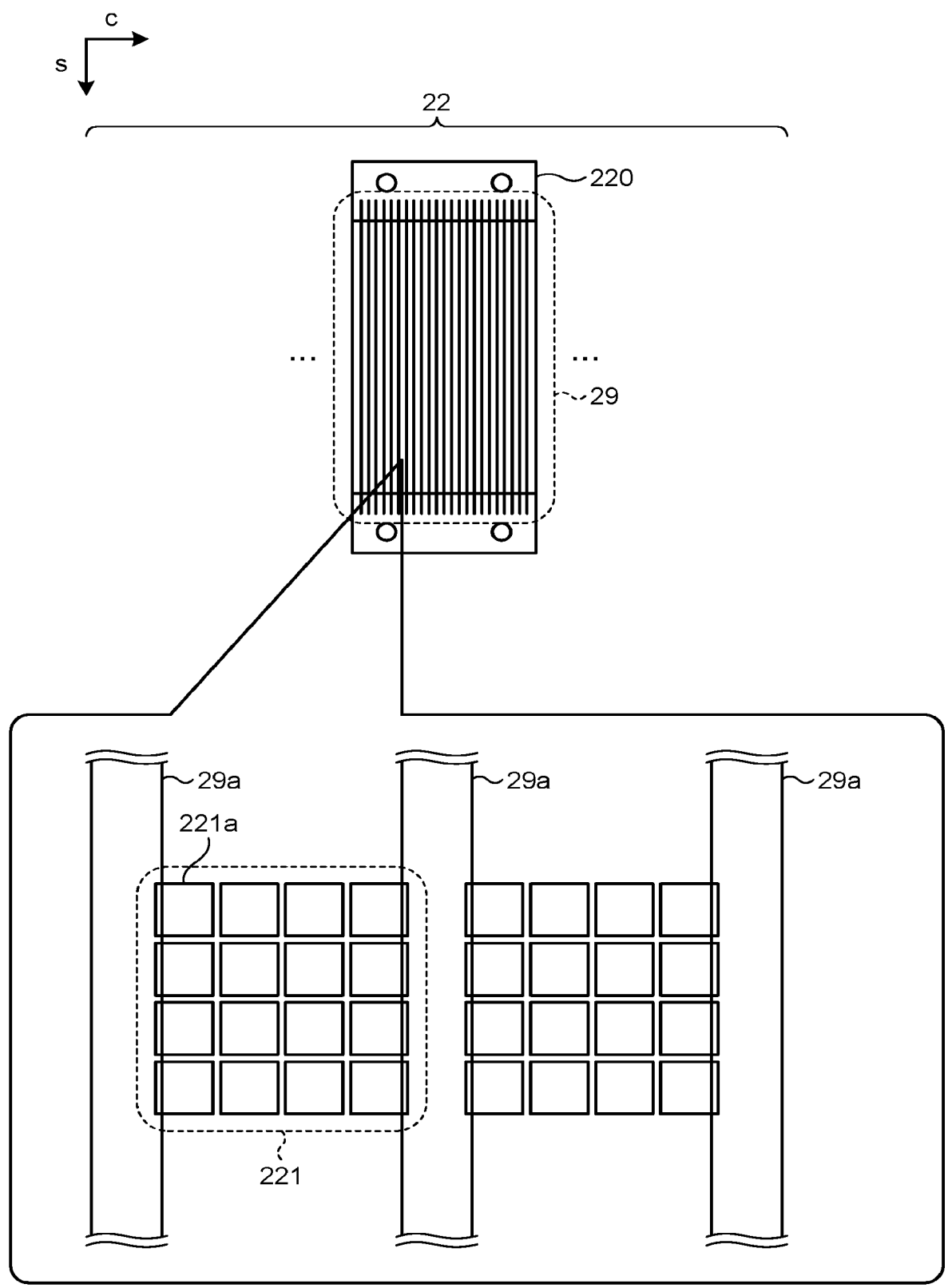
FIG. 2A and FIG. 2B are diagrams for explanation of misalignment according to the first embodiment.
Figure 2B:
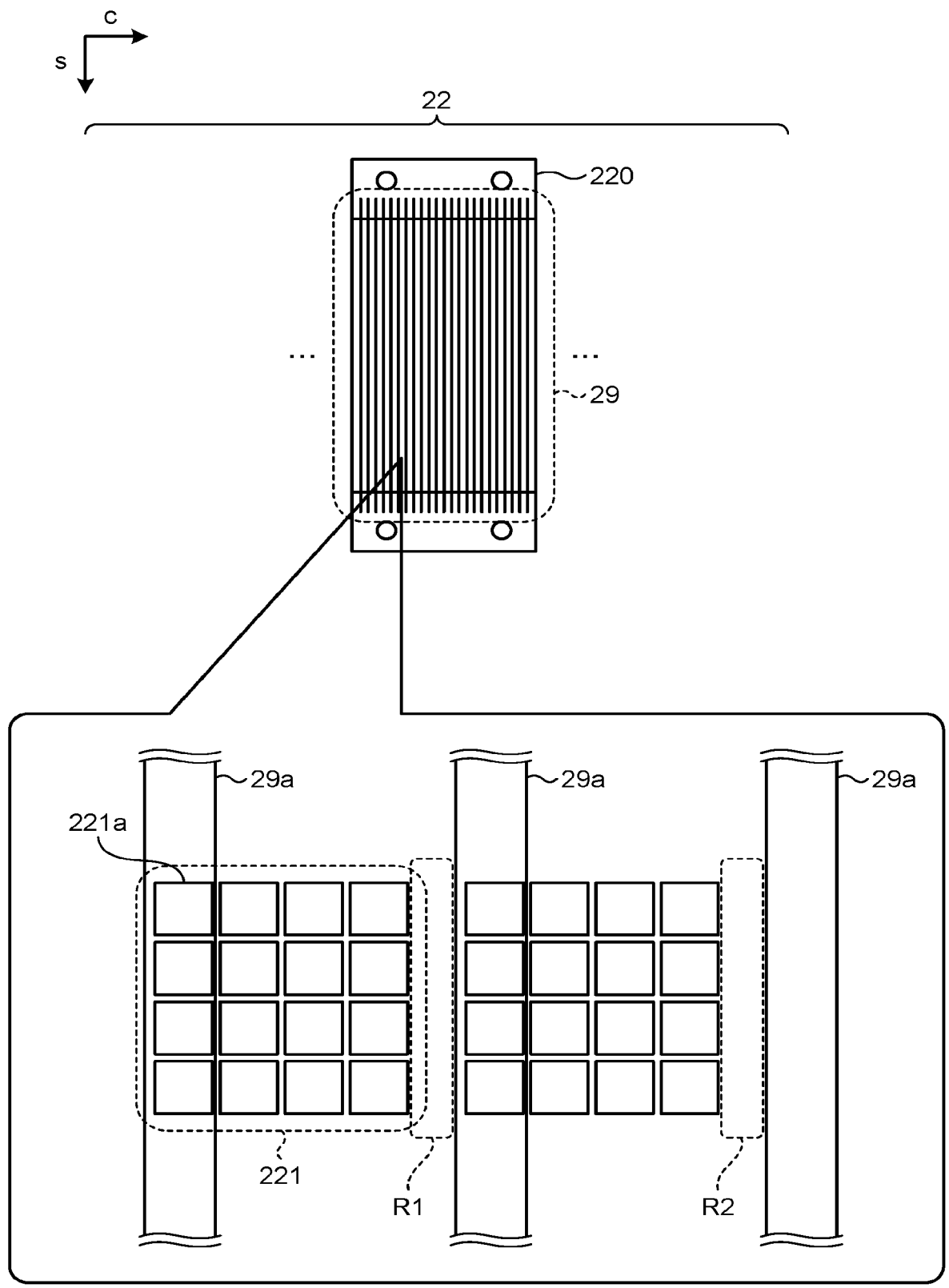

The X-ray diaphragm 17 is a lead plate for narrowing down the range irradiated with X-rays that have been transmitted through the wedge 16 and includes a combination of plural lead plates, the combination forming a slit. The X-ray diaphragm 17 may be called a pre-collimator. Furthermore, FIGS. 2A and 2B illustrate a case where the wedge 16 has been placed between the X-ray tube 11 and the X-ray diaphragm 17, but the X-ray diaphragm 17 may be placed between the X-ray tube 11 and the wedge 16 instead. If the X-ray diaphragm 17 is placed between the X-ray tube 11 and the wedge 16, the wedge 16 transmits and attenuates therethrough X-rays that have been emitted from the X-ray tube 11 and limited in their irradiation range by the X-ray diaphragm 17.

The X-ray high voltage generator 14 has: a high voltage generator that has an electric circuitry including a transformer and a rectifier and generates high voltage to be applied to the X-ray tube 11; and an X-ray controller that controls output voltage according to X-rays to be generated by the X-ray tube 11. The high voltage generator may be of the transformer-type or the inverter-type. The X-ray high voltage generator 14 may be provided on the rotating frame 13 or on a fixed frame not illustrated in the drawings.

The controller 15 has: a processing circuitry having a central processing unit (CPU); and a driving mechanism, such as a motor and an actuator. The controller 15 controls operation of the gantry 10 and the bed 30 by receiving input signals from an input interface 43. For example, the controller 15 controls rotation of the rotating frame 13, tilting of the gantry 10, and operation of the bed 30 and tabletop 33. In one example, the controller 15 performs control for tilting the gantry 10, the control including rotation of the rotating frame 13 about an axis parallel to the X-axis direction according to information on an inclination angle (a tilt angle) that has been input. The controller 15 may be provided on the gantry 10 or provided on the console 40.

Every time an X-ray photon enters the X-ray detector 12, the X-ray detector 12 outputs a signal enabling an energy value of the X-ray photon to be measured. The X-ray photon is, for example, an X-ray photon that has been emitted from the X-ray tube 11 and transmitted through the subject P. The X-ray detector 12 has plural detecting elements, each of which outputs an electric signal (an analog signal) of one pulse every time an X-ray photon enters that detecting element. Counting the number of electric signals (pulses) enables counting of the number of X-ray photons that have entered each of the detecting elements. Furthermore, performing predetermined arithmetic processing on these signals enables measurement of energy values of the X-ray photons that have caused the signals to be output. A collimator for reducing scattered X-rays is placed on one side of the X-ray detector 12, the one side being where the X-rays incident on the X-ray detector 12 are. The collimator may be called an anti-scatter grid or a post-collimator.

The above described detecting elements are each a sensor that is formed of plural electrodes and detects radiation. For example, the detecting elements each have the electrodes arranged on a semiconductor detecting element of cadmium telluride (CdTe) or cadmium zinc telluride (CdZnTe). That is, the X-ray detector 12 is a direct conversion detector that directly converts X-ray photons incident thereon into electric signals. This embodiment is not necessarily applied to the direct conversion detector, and is also applicable to an indirect conversion detector formed of a combination of a scintillator and a photodetector.

The X-ray detector 12 has: the above described detecting elements; and plural application specific integrated circuits (ASICs) that are connected to the detecting elements and count X-ray photons detected by the detecting elements. The ASICs count the numbers of X-ray photons that have entered the detecting elements by performing pulse height discrimination of electric pulses having heights proportional to individual electric charges output by the detecting elements. Furthermore, by performing arithmetic processing based on the individual electric charges, the ASICs measure energy of the X-ray photons that have been counted. In addition, the ASICs output, as digital data, results of the counting of the X-ray photons, to the DAS 18.

The DAS 18 generates detected data, based on the results of the counting input from the X-ray detector 12. The detected data are, for example, a sinogram. The sinogram is data having, arranged therein, the results of the counting for the incidence on the detecting elements at respective positions of the X-ray tube 11. The sinogram is data having the results of the counting arranged in a two-dimensional orthogonal coordinate system having axes along a view direction and a channel direction. The DAS 18 generates a sinogram, for example, row by row along a slice direction in the X-ray detector 12. The results of the counting are data having the numbers of X-ray photons assigned respectively to energy bins. For example, the DAS 18 counts photons (X-ray photons) originating from X-rays that have been emitted from the X-ray tube 11 and transmitted through the subject P, and determines results of the counting by discriminating energy values of the X-ray photons that have been counted. The DAS 18 transfers the detected data generated, to the console 40. The DAS 18 is implemented by, for example, a processor.

Data generated by the DAS 18 are transmitted, by optical communication, from a transmitter having a light emitting diode (LED) provided on the rotating frame 13, to a receiver provided on a non-rotating part (for example, a fixed frame, which is not illustrated in FIG. 1) of the gantry 10 and having a photodiode, and the transmitted data are transferred from the receiver to the console 40. The non-rotating part is, for example, the fixed frame that rotatably supports the rotating frame 13. The data from the rotating frame 13 to the non-rotating part of the gantry 10 are not necessarily transmitted by optical communication, and any non-contact type data transmission method may be adopted or a contact-type data transmission method may be adopted.

The bed 30 is a device on which the subject P to undergo imaging is placed and which moves the subject P, and has a base 31, a bed driving device 32, the tabletop 33, and a support frame 34. The base 31 is a housing that supports the support frame 34 movably in a vertical direction. The bed driving device 32 is a driving mechanism that moves the tabletop 33 having the subject P placed thereon, along a longitudinal direction of the tabletop 33, and includes a motor and an actuator. The tabletop 33 provided on an upper surface of the support frame 34 is a plate where the subject P is placed. The bed driving device 32 may move, in addition to the tabletop 33, the support frame 34 along the longitudinal direction of the tabletop 33.

The console 40 has a memory 41, a display 42, an input interface 43, and a processing circuitry 44. The console 40 is described as a device separate from the gantry 10, but the console 40 or a part of components of the console 40 may be included in the gantry 10.

The memory 41 is implemented by: a semiconductor memory element, such as a random access memory (RAM) or a flash memory; a hard disk; or an optical disk. The memory 41 stores therein, for example, projection data and/or CT image data. Furthermore, for example, the memory 41 stores therein a program for the circuitries included in the X-ray CT apparatus 1 to implement their functions. The memory 41 may be implemented by a server group (a cloud) connected to the X-ray CT apparatus 1 via a network.

The display 42 displays thereon various types of information. For example, the display 42 displays thereon various images generated by the processing circuitry 44 and/or displays thereon a graphical user interface (GUI) for receiving various operations from an operator. For example, the display 42 is a liquid crystal display or a cathode ray tube (CRT) display. The display 42 may be of the desktop type, or may be formed of a tablet terminal that is able to wirelessly communicate with the console 40.

The input interface 43 receives various input operations from the operator, converts the input operations received, into electric signals, and outputs the electric signals to the processing circuitry 44. Furthermore, for example, the input interface 43 receives, from the operator, operations for input of reconstruction conditions for reconstruction of CT image data and image processing conditions for generation of post-processed images from image data.

For example, the input interface 43 is implemented by any of: a mouse and a keyboard; a trackball; switches; buttons; a joystick; a touchpad enabling an input operation by a touch on an operation surface; a touchscreen having a display screen and a touchpad that have been integrated together; a non-contact input circuitry having an optical sensor used therein; and a voice input circuitry. The input interface 43 may be provided on the gantry 10. Furthermore, the input interface 43 may be formed of a tablet terminal that is able to wirelessly communicate with the console 40. In addition, the input interface 43 does not necessarily include physical operation parts, such as a mouse and a keyboard. For example, examples of the input interface 43 include an electric signal processing circuitry that receives an electric signal corresponding to an operation input from an external input device provided separately from the console 40 and outputs the electric signal to the processing circuitry 44.

The processing circuitry 44 controls the overall operation of the X-ray CT apparatus 1. For example, the processing circuitry 44 executes a system control function 441, a preprocessing function 442, a reconstruction processing function 443, an image processing function 444, a scan control function 445, and a display control function 446. Processing functions executed by the system control function 441, the preprocessing function 442, the reconstruction processing function 443, the image processing function 444, the scan control function 445, and the display control function 446, which are components of the processing circuitry 44 illustrated in FIG. 1, have been recorded, each in a form of a program that is able to be executed by a computer, in the memory 41. The processing circuitry 44 is, for example, a processor, reads these programs from the memory 41, and implements the functions corresponding to the read programs by executing the read programs. In other words, the processing circuitry 44 that has read the programs has the respective functions illustrated in the processing circuitry 44 in FIG. 1.

FIG. 1 illustrates a case where the processing functions of the system control function 441, the preprocessing function 442, the reconstruction processing function 443, the image processing function 444, the scan control function 445, and the display control function 446 are implemented by the single processing circuitry 44, but the embodiment is not limited to this case. For example, the processing circuitry 44 may be formed of a combination of plural independent processors and the processing functions may be implemented by these processors executing the respective programs. Furthermore, any of the processing functions that the processing circuitry 44 has may be implemented by being distributed to plural processing circuitries or being integrated into a single processing circuitry, as appropriate.

The system control function 441 controls various functions of the processing circuitry 44, based on input operations received from an operator via the input interface 43.

The preprocessing function 442 generates projection data by performing preprocessing, such as logarithmic transformation, offset correction, sensitivity correction between channels, and/or beam hardening correction, with respect to detected data output from the DAS 18.

The reconstruction processing function 443 generates CT image data by performing reconstruction processing using a filtered back projection method or a successive approximation reconstruction method, on the projection data generated by the preprocessing function 442. The reconstruction processing function 443 stores the reconstructed CT image data into the memory 41.

Projection data generated from results of counting acquired by photon counting CT include information on energy of X-rays attenuated by transmission through the subject P. Therefore, the reconstruction processing function 443 is able to reconstruct, for example, CT image data for a particular energy component. Furthermore, the reconstruction processing function 443 is able to reconstruct, for example, CT image data for each of plural energy components.

Moreover, the reconstruction processing function 443 is able to generate, for example, image data having plural sets of CT image data superimposed thereon, the plural sets of CT image data having been color coded according to energy components by assignment of color tones according to the energy components to pixels of the sets of CT image data for the respective energy components. What is more, the reconstruction processing function 443 is able to generate, for example, image data enabling identification of a substance by using a K absorption edge specific to the substance. Examples of other image data generated by the reconstruction processing function 443 include homogeneous X-ray image data, density image data, and effective atomic number image data.

Reconstructing CT image data requires projection data corresponding to one round around a subject, 360°, or projection data corresponding to "180°+fan angle" in a half scan method. This embodiment is applicable to any of these reconstruction methods. Hereinafter, a reconstruction (full scan reconstruction) method in which projection data corresponding to one round around a subject, 360°, is assumed to be used for simplification of explanation.

Based on an input operation received from an operator via the input interface 43, the image processing function 444 converts CT image data generated by the reconstruction processing function 443 into image data, such as a tomographic image of an arbitrary cross section or a three-dimensional image resulting from rendering processing, by using a known method. The image processing function 444 stores the converted image data into the memory 41.

The scan control function 445 controls CT scanning performed at the gantry 10. For example, the scan control function 445 controls collection of results of counting at the gantry 10, by controlling operation of the X-ray high voltage generator 14, the X-ray detector 12, the controller 15, the DAS 18, and the bed driving device 32. For example, the scan control function 445 controls each of: imaging for collection of position determining images (scanograms); and collection of projection data in actual imaging (scanning) for collection of images used in diagnosis.

The display control function 446 performs control such that various image data stored in the memory 41 are displayed on the display 42.

A configuration of the X-ray CT apparatus 1 according to the first embodiment has been described above. The X-ray CT apparatus 1 configured as described above has a configuration described below to reduce influence of misalignment.

This misalignment will be described by use of FIG. 2A and FIG. 2B. FIG. 2A and FIG. 2B are diagrams for explanation of misalignment according to the first embodiment. Upper diagrams in FIG. 2A and FIG. 2B exemplify diagrams where an X-ray detector 22 is viewed from one side of the X-ray detector 22, the one side being where X-rays incident on the X-ray detector 22 are. Furthermore, lower diagrams in FIG. 2A and FIG. 2B exemplify enlarged views of detecting elements in the upper diagrams. FIG. 2A is an example of a case where misalignment has not occurred, and FIG. 2B is an example of a case where misalignment has occurred. Furthermore, in FIG. 2A and FIG. 2B, "c" corresponds to a channel direction and "s" corresponds to a slice direction.

Similarly to the X-ray detector 12 according to the embodiment, the X-ray detector 22 is a direct conversion detector. For example, as illustrated in the upper diagrams of FIG. 2A and FIG. 2B, the X-ray detector 22 has plural detector modules 220 arranged in the channel direction. A collimator 29 for reducing scattered X-rays is placed on one side of the detector modules 220, the one side being where X-rays incident on the detector modules 220 are. The collimator 29 has a structure having plural shielding plates 29a arranged in the channel direction. The shielding plates 29a have a function of absorbing scattered X-rays and are arranged parallel to a plane that is along the incident direction of X-rays and the slice direction.

As illustrated in the lower diagram of FIG. 2A, when misalignment has not occurred, for example, one detecting element 221 is placed each between the respective shielding plates 29a. This detecting element 221 is formed, for example, in a square shape having a side of about 500 μm and has a total of 16 electrodes 221a (anodes), four each along the channel direction and the slice direction. Two detecting elements 221 are illustrated each in FIG. 2A and FIG. 2B, but two or more detecting elements 221 are actually arranged in the channel direction and the slice direction.

If misalignment has occurred, the shielding plates 29a obstruct the paths of X-rays on some of the electrodes 221a. In the example illustrated in the lower diagram of FIG. 2B, the paths of X-rays on one row of the electrodes 221a arranged in the slice direction have been obstructed. Furthermore, although X-rays will enter regions R1 and R2, because no electrodes 221a are present in the regions R1 and R2, dead space will be created in these regions R1 and R2. As described above, if misalignment occurs, X-rays will not be able to be detected sufficiently and the image quality is thus influenced by the insufficient detection.

Furthermore, in recent years, precision required for alignment tolerance is increasing, because the proportion of the amount of displacement to the detecting element size has increased due to the improvement in the spatial resolution of radiation detectors. For example, higher resolution where one side is less than 500 μm is able to be achieved by the X-ray detector 12 for photon counting computed tomography (CT), and precision required for its alignment tolerance is thus high. However, performing high precision alignment for each of its plural detector modules is difficult.

Accordingly, the X-ray CT apparatus 1 according to the first embodiment has the configuration described below, for reduction of influence of misalignment.

Figure 3A:
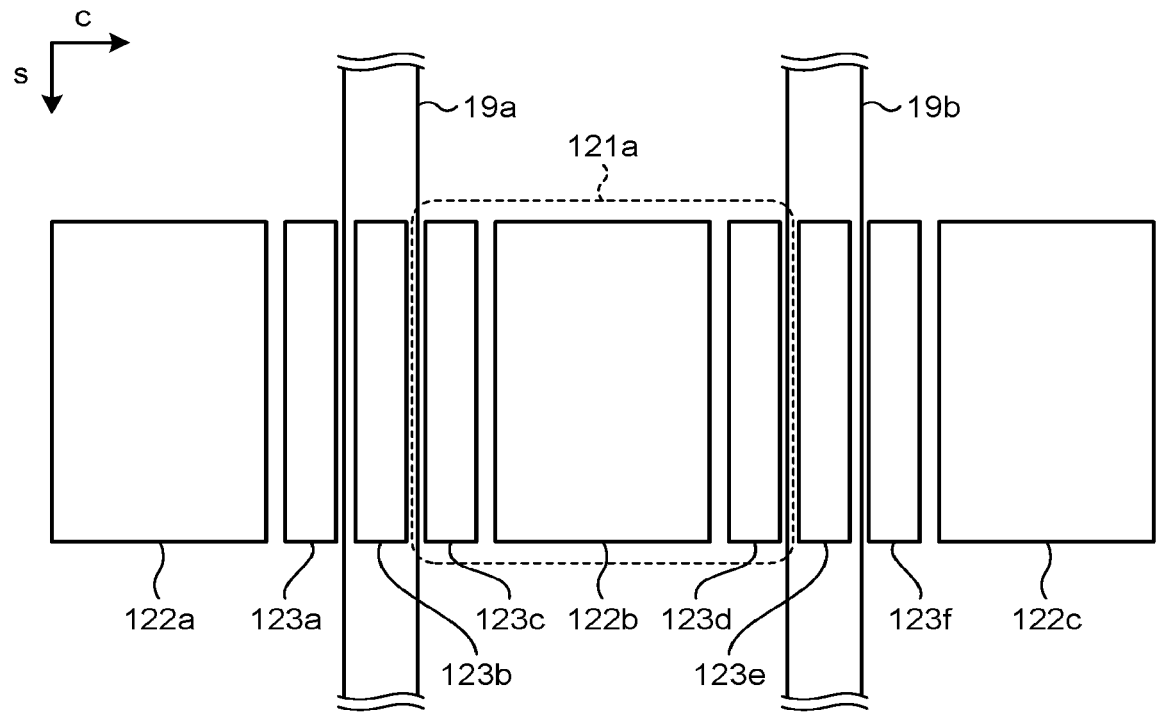
FIG. 3A to FIG. 3C are diagrams illustrating an example of a configuration of an X-ray detector according to the first embodiment.
Figure 3B:
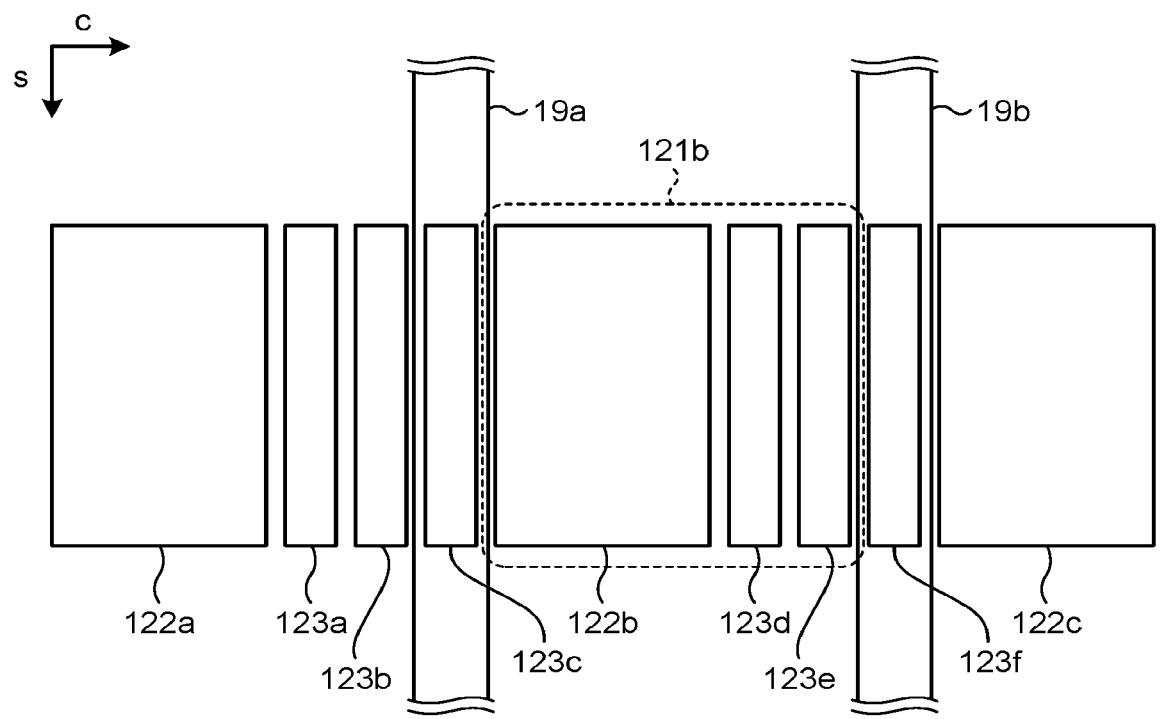
Figure 3C:
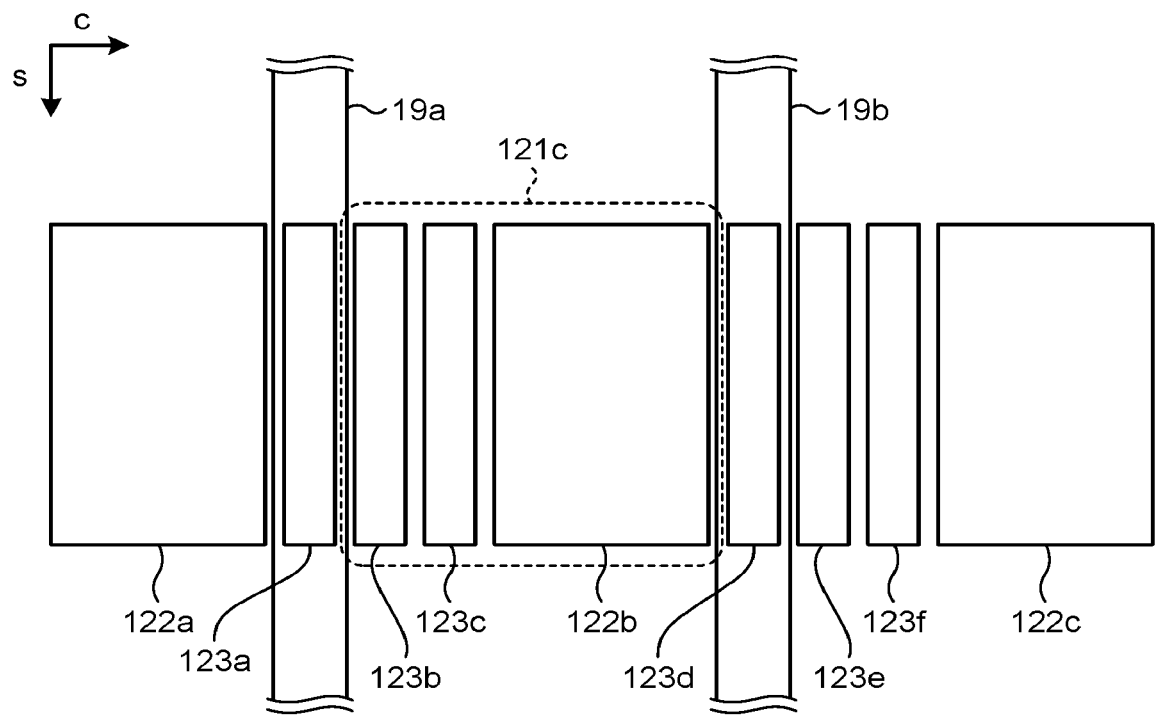

The configuration of the X-ray detector 12 according to the first embodiment will be described by use of FIG. 3A, FIG. 3B, and FIG. 3C. FIG. 3A, FIG. 3B, and FIG. 3C are diagrams illustrating an example of the configuration of the X-ray detector 12 according to the first embodiment. FIG. 3A, FIG. 3B, and FIG. 3C exemplify arrangement of electrodes (anodes) forming a detecting element in the X-ray detector 12. FIG. 3A is an example of a case where misalignment has not occurred. FIG. 3B is an example of a case where a collimator has been misaligned in a positive direction along the channel direction. FIG. 3C is an example of a case where the collimator has been misaligned in a negative direction along the channel direction. Furthermore, in FIG. 3A, FIG. 3B, and FIG. 3C, "c" corresponds to the channel direction and "s" corresponds to the slice direction.

Similarly to the X-ray detector 22 illustrated in the upper diagrams of FIG. 2A and FIG. 2B, the X-ray detector 12 has plural detector modules 120 arranged in the channel direction, and a collimator 19 for reducing scattered X-rays is placed on one side of each of the detector modules 120, the one side being where X-rays incident on the detector modules 120 are. Similarly to the collimator 29, the collimator 19 has a structure with plural shielding plates 19a and 19b arranged in the channel direction. The shielding plates 19a and 19b have a function of absorbing scattered X-rays and are arranged parallel to a plane that is along the incident direction of X-rays and the slice direction. Since the positional relation between the detector modules 120 and the collimators 29 is the same as the positional relation between the detector modules 220 and the collimators 29 illustrated in the upper diagrams of FIG. 2A and FIG. 2B, illustration thereof will be omitted.

As illustrated in FIG. 3A, FIG. 3B, and FIG. 3C, the X-ray detector 12 has plural main electrodes 122a, 122b, and 122c, and plural sub-electrodes 123a, 123b, 123c, 123d, 123e, and 123f. When the plural main electrodes 122a, 122b, and 122c are generally referred to without distinction among them, they will be referred to as the "main electrodes 12". Furthermore, when the plural sub-electrodes 123a, 123b, 123c, 123d, 123e, and 123f are generally referred to without distinction among them, they will be referred to as the "sub-electrodes 123". The main electrodes 122 are each an example of a first electrode. The sub-electrodes 123 are each an example of a second electrode.

The main electrodes 122 and the sub-electrodes 123 are electrodes placed on the anode side of the semiconductor detecting elements. The main electrodes 122 are main electrodes forming the detecting elements and are arranged two-dimensionally in the channel direction and the slice direction. Furthermore, the sub-electrodes 123 are electrodes smaller than the main electrodes 122 and plural ones of the sub-electrodes 123 are provided between plural ones of the main electrodes 122. For example, in the illustrated example, the sub-electrodes 123 are arranged three each between the main electrodes 122 that are adjacent to each other in the channel direction.

As illustrated in FIG. 3A, if misalignment has not occurred, the shielding plate 19a is positioned on the X-ray path of the sub-electrode 123b and the shielding plate 19b is positioned on the X-ray path of the sub-electrode 123e. In this case, one main electrode 122b and two sub-electrodes 123c and 123d form one detecting element 121a.

Furthermore, as illustrated in FIG. 3B, if the collimator 19 is misaligned in a positive direction along the channel direction, the shielding plate 19a is positioned on the X-ray path of the sub-electrode 123c and the shielding plate 19b is positioned on the X-ray path of the sub-electrode 123f. In this case, one main electrode 122b and two sub-electrodes 123d and 123e form one detecting element 121b.

Furthermore, as illustrated in FIG. 3C, if the collimator 19 is misaligned in a negative direction along the channel direction, the shielding plate 19a is positioned on the X-ray path of the sub-electrode 123a and the shielding plate 19b is positioned on the X-ray path of the sub-electrode 123d. In this case, one main electrode 122b and two sub-electrodes 123b and 123c form one detecting element 121b.

Specifically, based on the positional relation between the plural electrodes and the collimator 19, the X-ray detector 12 performs control (switch control) for changing electrodes forming a detecting element. As a result, the X-ray detector 12 is able to reduce influence of misalignment. Although one detecting element is illustrated in each of FIG. 3A, FIG. 3B, and FIG. 3C, plural detecting elements are actually arranged in the channel direction and the slice direction.

Figure 4:
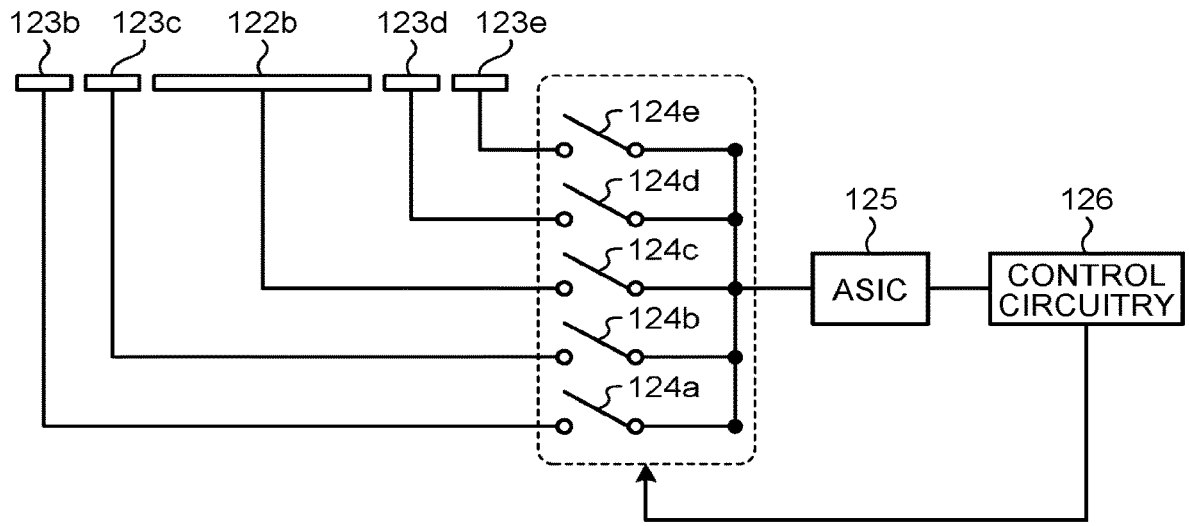
FIG. 4 is a diagram for explanation of switch control of electrodes according to the first embodiment.

Next, switch control of electrodes according to the first embodiment will be described by use of FIG. 4. FIG. 4 is a diagram for explanation of switch control of electrodes according to the first embodiment. As illustrated in FIG. 4, the X-ray detector 12 has switches 124a, 124b, 124c, 124d, and 124e, an ASIC 125 and a control circuitry 126, which are downstream from plural electrodes.

The switches 124a, 124b, 124c, 124d, and 124e are respectively provided between the electrodes and the ASIC 125. In the example illustrated in FIG. 4, the switch 124a is provided between the sub-electrode 123b and the ASIC 125. The switch 124b is provided between the sub-electrode 123c and the ASIC 125. The switch 124c is provided between the main electrode 122b and the ASIC 125. The switch 124d is provided between the sub-electrode 123d and the ASIC 125. The switch 124e is provided between the sub-electrode 123e and the ASIC 125. Furthermore, signal lines from the switches 124a, 124b, 124c, 124d, and 124e are bundled and connected to the single ASIC 125. When the plural switches 124a, 124b, 124c, 124d, and 124e are generally referred to without distinction among them, they will be referred to as the "switches 124".

The ASIC 125 is an electronic circuitry that outputs digital data, based on signals output from the electrodes. For example, the ASIC 125 bundles signals output from the plural electrodes (the main electrode 122 and the sub-electrodes 123) and measures the signals bundled as output from a single detecting element. The ASIC 125 then outputs results of counting of the X-ray photons as digital data, to the DAS 18.

The control circuitry 126 is formed of a processing circuitry having a CPU, and controls the switches 124, based on the positional relation between the plural electrodes and the collimator 19. For example, the control circuitry 126 performs control for switching on or off the plural switches 124 according to three connection patterns (connection patterns A, B, and C).

According to the connection pattern A, the switch 124a is turned "OFF", the switch 124b is turned "ON", the switch 124c is turned "ON", the switch 124d is turned "ON", and the switch 124e is turned "OFF". In this case, because the main electrode 122b and the two sub-electrodes 123c and 123d are connected to the ASIC 125, the detecting element 121a illustrated in FIG. 3A is formed.

According to the connection pattern B, the switch 124a is turned "OFF", the switch 124b is turned "OFF", the switch 124c is turned "ON", the switch 124d is turned "ON", and the switch 124e is turned "ON". In this case, because the main electrode 122b and the two sub-electrodes 123d and 123e are connected to the ASIC 125, the detecting element 121b illustrated in FIG. 3B is formed.

According to the connection pattern C, the switch 124a is turned "ON", the switch 124b is turned "ON", the switch 124c is turned "ON", the switch 124d is turned "OFF", and the switch 124e is turned "OFF". In this case, because the main electrode 122b and the two sub-electrodes 123b and 123c are connected to the ASIC 125, the detecting element 121c illustrated in FIG. 3C is formed.

That is, the control circuitry 126 bundles signals output respectively from the main electrode 122 and the sub-electrodes 123 included in each detecting element, by outputting the signals output from the main electrode 122 and the sub-electrodes 123 to the ASIC 125 common thereto.

The control circuitry 126 compares outputs from the detecting elements for the respective connection patterns. For example, the control circuitry 126 causes the ASIC 125 to count the number of photons per unit time for each of the three connection patterns (the connection patterns A, B, and C) and to store the counted number in a memory inside the X-ray detector 12. The control circuitry 126 then compares the number of photons for the connection pattern A, the number of photons for the connection pattern B, and the number of photons for the connection pattern C, with one another.

It is considered that the number of photons for the connection pattern A becomes the largest if misalignment has not occurred. Furthermore, it is considered that the number of photons for the connection pattern B becomes the largest if the collimator 19 has been misaligned in the positive direction along the channel direction. In addition, it is considered that the number of photons for the connection pattern C becomes the largest if the collimator 19 has been misaligned in the negative direction along the channel direction.

Therefore, the control circuitry 126 turns on or off the switches 124 in the connection pattern for which the whole number of photons becomes the largest as a result of the comparison. Specifically, the control circuitry 126 controls the switches 124 between the sub-electrodes 123 and the ASIC 125.

As described above, based on the signals output from the detecting elements, the control circuitry 126 controls the switches 124. As a result, even if misalignment occurs, the control circuitry 126 changes the detecting element to be connected according to the misalignment and reads signals from plural electrodes corresponding to the misaligned position, and influence of the misalignment is thus able to be reduced.

FIG. 4 illustrates one ASIC 125 for convenience of explanation, but the X-ray detector 12 actually includes a plurality of the ASICs 125. For example, the X-ray detector 12 preferably includes the same number of ASICs 125 as the number of detecting elements (the number of main electrodes 122) forming the X-ray detector 12.

Furthermore, FIG. 4 illustrates a case where an appropriate connection pattern is automatically selected from the plural connection patterns, but the embodiment is not limited to this case. For example, an operator may check the positional relation between the electrodes and the collimator 19 by visual observation and specify information indicating the checked positional relation. In this case, based on the positional relation specified by the operator, the control circuitry 126 controls the switches 124.

Furthermore, FIG. 4 illustrates a case where the connection patterns are prescribed, but the embodiment is not limited to this case. For example, the control circuitry 126 may arbitrarily turn the switches 124 on or off according to operation by an operator. However, the number of ASICs 125 connected to each electrode during operation of the X-ray detector 12 is one.

Furthermore, the control circuitry 126 is able to execute switch control at any time. For example, the control circuitry 126 preferably performs the above described switch control every time alignment of the collimators 19 over the detector modules 120 is performed, but the embodiment is not limited to this example. For example, the control circuitry 126 may periodically perform the switch control (for example, every day or every week), or may perform the switch control at any time during imaging.

As described above, the detecting elements in the X-ray detector 12 according to the first embodiment are each formed of plural electrodes and detect radiation. Based on signals output from the electrodes, the ASIC 125 outputs digital data. The switches 124 are provided respectively for the electrodes, between the electrodes and the ASIC 125. Based on the positional relation between the plural electrodes and the collimator 19, the control circuitry 126 performs feedback control of the switches 124. As a result, the X-ray detector 12 is able to reduce influence of misalignment.

Furthermore, when the X-ray detection efficiency is reduced due to misalignment, unwanted exposure of the subject to radiation is increased. The X-ray detector 12 according to the first embodiment enables less reduction in the X-ray detection efficiency due to misalignment and thus enables unwanted exposure to radiation.

First Modification of First Embodiment

Figure 5:
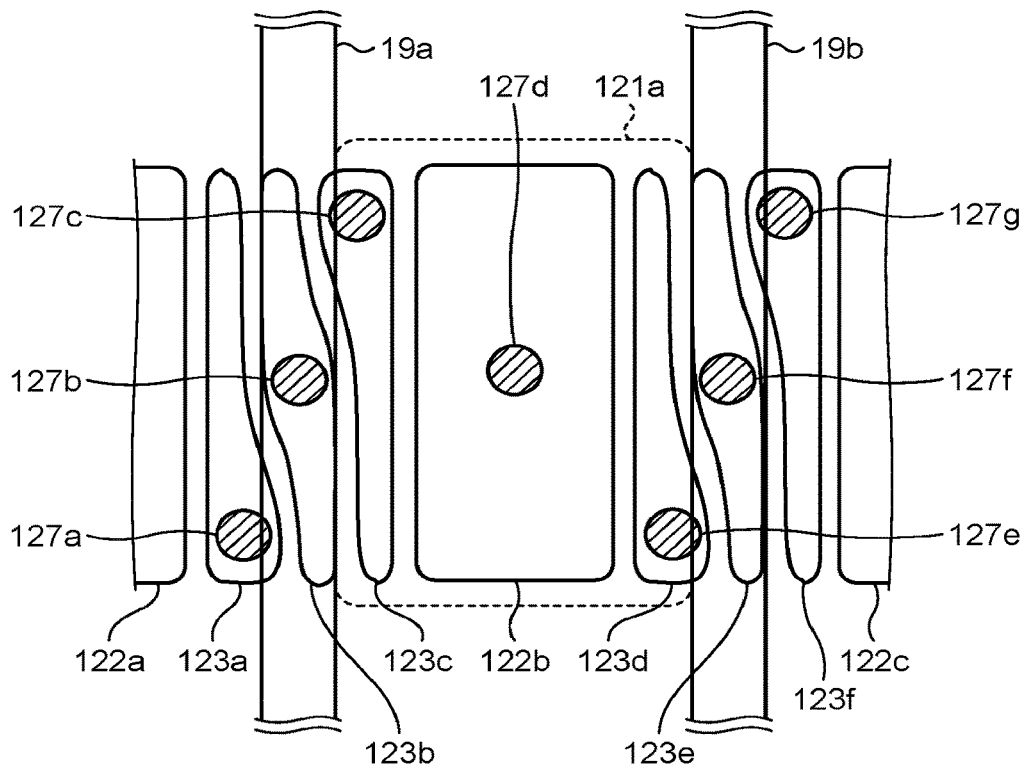
FIG. 5 is a diagram illustrating an example of a configuration of an X-ray detector according to a first modification of the first embodiment.

Another example of arrangement of plural electrodes will be described. FIG. 5 is a diagram illustrating an example of a configuration of an X-ray detector 12 according to a first modification of the first embodiment. FIG. 5 exemplifies arrangement of electrodes (anodes) forming a detecting element in the X-ray detector 12. Furthermore, in FIG. 5, "c" corresponds to a channel direction and "s" corresponds to a slice direction.

As illustrated in FIG. 5, the X-ray detector 12 has plural main electrodes 122a, 122b, and 122c and plural sub-electrodes 123a, 123b, 123c, 123d, 123e, and 123f. Furthermore, each of these electrodes has a bump 127 connected to a switch 124. Specifically, a bump 127a is formed on the sub-electrode 123a, a bump 127b is formed on the sub-electrode 123b, a bump 127c is formed on the sub-electrode 123c, a bump 127d is formed on the main electrode 122b, a bump 127e is formed on the sub-electrode 123d, a bump 127f is formed on the sub-electrode 123e, and a bump 127g is formed on the sub-electrode 123f. When the plural bumps 127a, 127b, 127c, 127d, 127e, 127f, and 127g are generally referred to without distinction among them, they will be referred to as the "bumps 127". The bumps 127 are each an example of a joint portion.

The bumps 127 on two adjacent ones of the sub-electrodes 123 are displaced from each other in a direction different from the arrangement direction of a shielding plate 19a and a shielding plate 19b, the arrangement direction being the channel direction. For example, the bump 127a and the bump 127b are arranged to be displaced from each other in the slice direction. Furthermore, the bump 127b and the bump 127c are arranged to be displaced from each other in the slice direction. As a result, the detecting element 121a is able to be increased in resolution.

The increase of the resolution of this detecting element will be described. In general, as the electrodes and the bumps 127 are decreased in size, the detecting element is able to be increased in resolution, but the minimum size of the bumps 127 is limited to some extent. Therefore, when the plural sub-electrodes 123 are arranged side by side in the channel direction, the width of each sub-electrode 123 needs to be made larger than the minimum size of the bumps 127.

However, according to the embodiment, when the sub-electrodes 123a, 123b, and 123c are arranged in the channel direction, the bumps 127 on the sub-electrodes 123 are arranged to be displaced from one another in the slice direction. As a result, the width of each of the sub-electrodes 123a, 123b, and 123c is able to be made partially smaller than the minimum size of the bumps 127.

Second Modification of First Embodiment

With respect to the first embodiment, a case where the collimators 19 are one-dimensional collimators has been described, but the first embodiment is not limited to this case. For example, even if the collimators 19 are two-dimensional collimators, influence of misalignment is able to be reduced.

Figure 6:
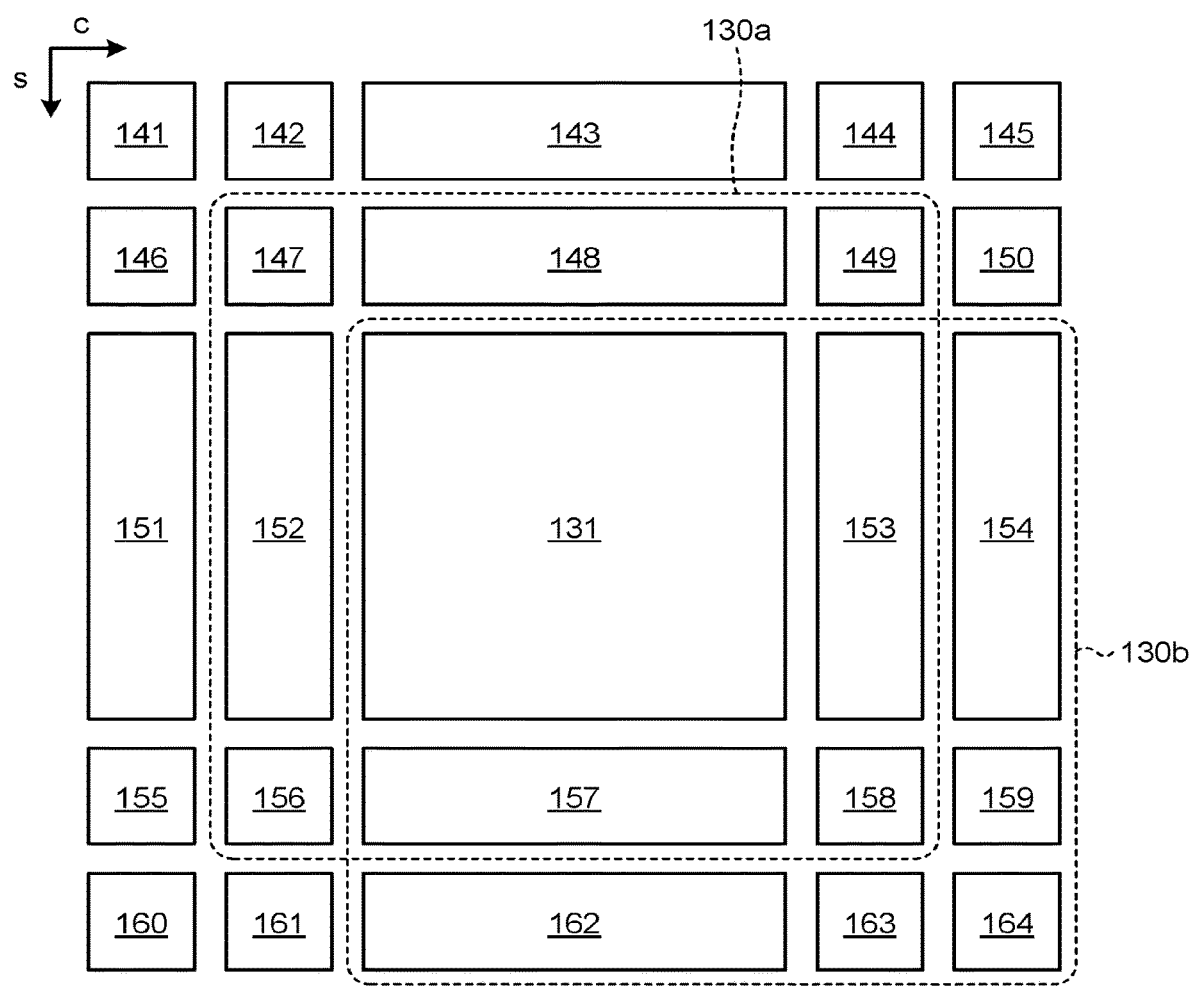
FIG. 6 is a diagram illustrating an example of a configuration of an X-ray detector according to a second modification of the first embodiment.

FIG. 6 is a diagram illustrating an example of a configuration of an X-ray detector 12 according to a second modification of the first embodiment. FIG. 6 exemplifies arrangement of electrodes (anodes) forming a detecting element in the X-ray detector 12. Furthermore, in FIG. 6, "c" corresponds to a channel direction and "s" corresponds to a slice direction.

As illustrated in FIG. 6, the X-ray detector 12 has a main electrode 131 and plural sub-electrodes 141, 142, 143, 144, 145, 146, 147, 148, 149, 150, 151, 152, 153, 154, 155, 156, 157, 158, 159, 160, 161, 162, 163, and 164. Furthermore, these electrodes are connected to an ASIC 125 via switches 124, although this connection is not illustrated in the drawings.

For example, when misalignment has not occurred, the main electrode 131 and eight of the sub-electrodes 147, 148, 149, 152, 153, 156, 157, and 158 form a detecting element 130a. In this case, a control circuitry 126 forms the detecting element 130a by turning on the switches 124 connected to the main electrode 131 and the eight sub-electrodes 147, 148, 149, 152, 153, 156, 157, and 158 and turning off the other switches.

Furthermore, for example, if the collimator 19 has been misaligned in a positive direction along the channel direction and a positive direction along the slice direction, the main electrode 131 and eight of the sub-electrodes 153, 154, 157, 158, 159, 162, 163, and 164 form a detecting element 130b. In this case, the control circuitry 126 forms the detecting element 130b by turning on the switches 124 connected to the main electrode 131 and the eight sub-electrodes 153, 154, 157, 158, 159, 162, 163, and 164 and turning off the other switches.

Accordingly, even when two-dimensional collimators are used for the X-ray detector 12, influence of misalignment in each of the channel direction and the slice direction is able to be reduced, too.

Third Modification of First Embodiment

With respect to the first embodiment, a case where the plural electrodes include plural types of electrodes (the main electrode 122 and the sub-electrodes 123) having different sizes has been described, but the first embodiment is not limited to this case. For example, the plural electrodes may be plural electrodes having a uniform size.

Figure 7:
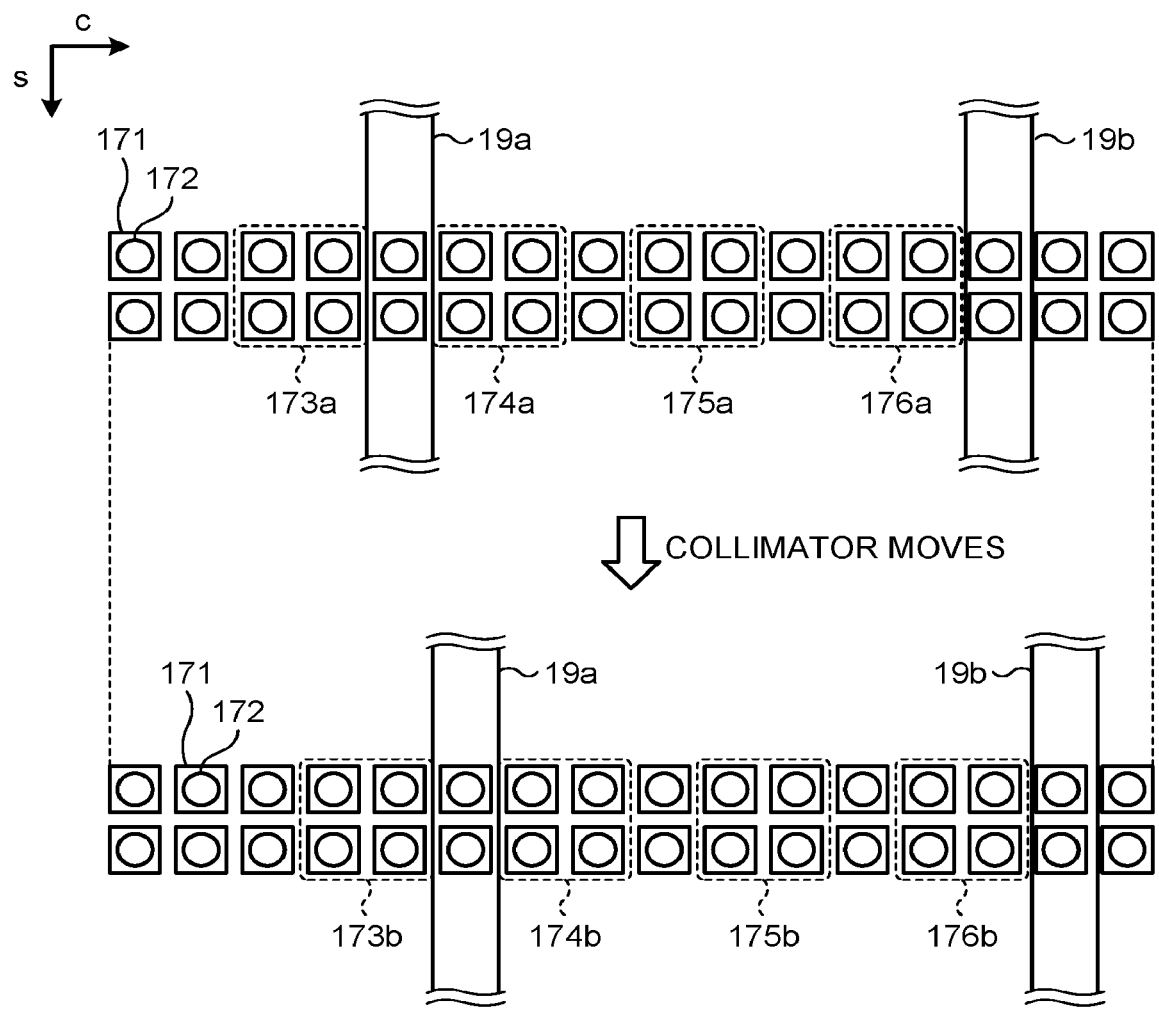
FIG. 7 is a diagram illustrating an example of a configuration of an X-ray detector according to a third modification of the first embodiment.

FIG. 7 is a diagram illustrating an example of a configuration of an X-ray detector 12 according to a third modification of the first embodiment. FIG. 7 exemplifies arrangement of electrodes (anodes) forming a detecting element in the X-ray detector 12. The lower diagram in FIG. 7 illustrates a case where a collimator in the upper diagram in FIG. 7 has moved in a positive direction along a channel direction. Furthermore, in FIG. 7, "c" corresponds to the channel direction and "s" corresponds to a slice direction. For convenience of illustration, FIG. 7 exemplifies electrodes 171 arranged in two rows in the slice direction, but two or more electrodes 171 are actually arranged in the channel direction and the slice direction.

As illustrated in FIG. 7, the X-ray detector 12 has plural electrodes 171 having a uniform size. For example, the electrodes 171 are each formed in a smallest size that is able to include a bump 172 of a smallest size. In the example illustrated in FIG. 7, sixteen electrodes 171 are arranged between a shielding plate 19a and a shielding plate 19b.

In the upper diagram of FIG. 7, detecting elements 173a, 174a, 175a, and 176a are formed. In this case, a control circuitry 126 forms the detecting elements 173a, 174a, 175a, and 176a, by turning on switches 124 connected to the electrodes 171 included in the detecting elements 173a, 174a, 175a, and 176a and turning off the other switches.

As illustrated in the lower diagram of FIG. 7, when the collimator has been displaced in the positive direction along the channel direction, the electrodes forming the detecting elements are changed according to this displacement. In this case, the control circuitry 126 forms detecting elements 173b, 174b, 175b, and 176b by shifting the detecting elements 173a, 174a, 175a, and 176a according to the moving distance of the collimator. The control circuitry 126 forms the detecting elements 173b, 174b, 175b, and 176b, by turning on switches 124 connected to the electrodes 171 included in the detecting elements 173b, 174b, 175b, and 176b and turning off the other switches.

Accordingly, by the electrodes being made uniform in size and each having the smallest size that is able to include the bump 172 of the smallest size, the X-ray detector 12 enables higher resolution detection as compared to the interval between the shielding plates. The number of electrodes forming each detecting element is not limited to the ones illustrated in the drawings and may be set at any number.

Second Embodiment

With respect to the first embodiment, a case where influence of misalignment between the X-ray detector 12 and the collimators 19 is reduced has been described, but the first embodiment is not limited to this case. For example, misalignment may occur due to change in the focal position of the X-rays (a flying focus). Therefore, with respect to a second embodiment, a case where an X-ray CT apparatus 1 dynamically performs switch control when a flying focus is adopted will be described.

Figure 8:
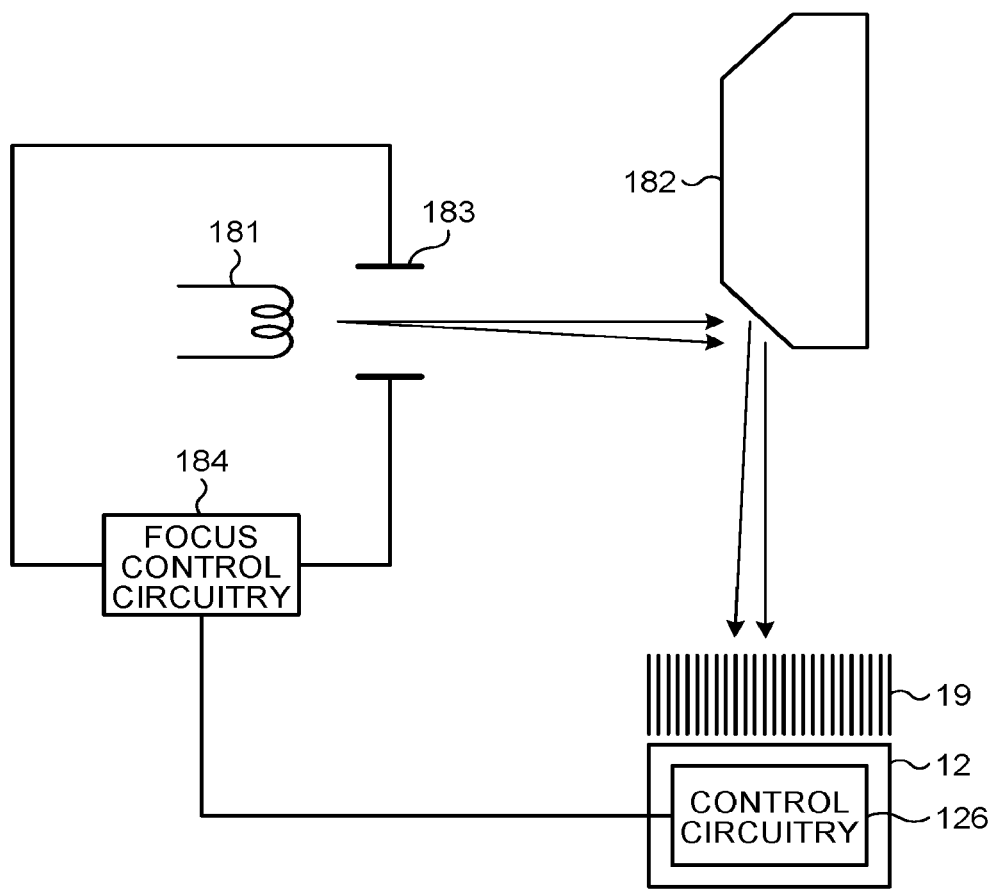
FIG. 8 is a diagram for explanation of processing by a control circuitry according to a second embodiment.

FIG. 8 is a diagram for explanation of processing by a control circuitry 126 according to the second embodiment. As illustrated in FIG. 8, an X-ray tube 11 has a filament (a cathode) 181, a target (an anode) 182, a grid 183, and a focus control circuitry 184.

The filament 181 emits thermions. The target 182 receives the thermions emitted from the filament 181 and generates X-rays. The focus control circuitry 184 changes the focus of the X-rays by controlling the position of irradiation of the target 182 with the thermions emitted from the filament 181. For example, the focus control circuitry 184 changes the focal position of X-rays by electromagnetic deflection, by controlling voltage applied to the grid 183. A known technique may be selected and applied as appropriate as a method of changing the focal position through a flying focus.

If two focal positions "F1" and "F2" different from each other exist, their relative positional relations (alignments) to collimators 19 and an X-ray detector 12 may be different from each other. Therefore, the control circuitry 126 stores connection patterns corresponding respectively to these focal positions beforehand. These connection patterns are prescribed by comparison among outputs from detecting elements (for example, the numbers of photons) beforehand.

If a flying focus is adopted during imaging, the control circuitry 126 refers to the imaging conditions (for example, the voltage profile), reads the timing for change of the focal position, and turns switches 124 on or off in a connection pattern corresponding to a focal position, according to the timing read.

As described above, based on a positional relation of the detecting elements and the collimator 19 to the focal position of X-rays changed by the focus control circuitry 184, the control circuitry 126 controls the switches 124. As a result, the X-ray CT apparatus 1 according to the second embodiment is able to dynamically perform switch control according to change in the focal position of X-rays.

Other Embodiments

Various different embodiments may be implemented in addition to the embodiments described above.

Furthermore, the components of the apparatuses have been functionally and conceptually illustrated in the drawings and are not necessarily configured physically as illustrated in the drawings. That is, specific forms of distribution and integration of the apparatuses are not limited to those illustrated in the drawings, and all or a part of each apparatus may be configured to be distributed or integrated functionally or physically in any units, according to various loads and/or use situations. In addition, all or any part of the processing functions executed in the apparatuses may be implemented by a CPU and a program analyzed and executed by the CPU or implemented as hardware by wired logic.

Furthermore, among the processing described with respect to the embodiments and modifications described above, all or a part of the processing described as being performed automatically may be performed manually, or all or a part of the processing described as being performed manually may be performed automatically by a known method. In addition, the processing procedures, control procedures, specific names, and information including various data and parameters, which have been described above and illustrated in the drawings may be arbitrarily modified except otherwise described specifically.

According to at least one of the embodiments described above, influence of misalignment is able to be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation detector, comprising:
   a sensor configured to be formed of plural electrodes and detect radiation;
   an electronic circuitry configured to output digital data, based on signals output from the electrodes;
   a switch configured to be provided between each of the electrodes and the electronic circuitry; and
   a control circuitry configured to control the switch, based on a positional relation between the plural electrodes and an anti-scatter grid.

2. The radiation detector according to claim 1, wherein the control circuitry controls the switch, based on the output of the signals from the sensor.

3. The radiation detector according to claim 1, wherein the control circuitry controls the switch, based on a positional relation of the sensor and the anti-scatter grid to a focal position of the radiation.

4. The radiation detector according to claim 1, wherein the sensor has a first electrode and a second electrode smaller than the first electrode, the first electrode and the second electrode serving as the plural electrodes, and the control circuitry controls the switch connected to the second electrode, based on the positional relation.

5. The radiation detector according to claim 4, wherein a plurality of the second electrodes are provided between a plurality of the first electrodes.

6. The radiation detector according to claim 5, wherein the second electrode has a joint portion connected to the switch, and
   the joint portions of two adjacent ones of the second electrodes are arranged to be displaced from each other in a direction different from an arrangement direction of plural shielding plates in the anti-scatter grid.

7. The radiation detector according to claim 4, wherein the control circuitry bundles signals respectively output from the first electrode and the second electrode included in each of the sensors, by causing the signals output from the first electrode and the second electrode to be output to the electronic circuitry common to the first electrode and the second electrode.

8. The radiation detector according to claim 1, wherein the sensor has the plural electrodes that are uniform in size.

9. An X-ray CT apparatus, comprising:
   a filament configured to emit thermions;
   a target configured to receive the thermions and generates X-rays;
   a focus control circuitry configured to change a focus of the X-rays by controlling a position of irradiation of the target with the thermions emitted from the filament;
   a sensor configured to be formed of plural electrodes and detect radiation;
   an electronic circuitry configured to output digital data, based on signals output from the electrodes; and
   a switch configured to be provided between each of the electrodes and the electronic circuitry; and
   a control circuitry configured to control the switch, based on a positional relation of the sensor and an anti-scatter grid to a focal position of the X-rays changed by the focus control circuitry.

* * * * *